(12) United States Patent
Deepa

(10) Patent No.: US 9,119,872 B2
(45) Date of Patent: Sep. 1, 2015

(54) GARLIC FORMULATION AND A PROCESS FOR PREPARING THE SAME FOR TREATMENT OF DIABETES

(71) Applicant: M. A. Deepa, Karnataka (IN)

(72) Inventor: M. A. Deepa, Karnataka (IN)

( * ) Notice: Subject to any disclaimer, the term of this patent is extended or adjusted under 35 U.S.C. 154(b) by 170 days.

(21) Appl. No.: 13/906,432

(22) Filed: May 31, 2013

(65) Prior Publication Data

US 2014/0147528 A1 May 29, 2014

(30) Foreign Application Priority Data

Nov. 26, 2012 (IN) .......................... 4920/CHE/2012

(51) Int. Cl.
*A61K 36/8962* (2006.01)

(52) U.S. Cl.
CPC ......... *A61K 36/8962* (2013.01); *A61K 2236/00* (2013.01)

(58) Field of Classification Search
USPC ......................................... 424/754
IPC ................................. A61K 36/8962
See application file for complete search history.

(56) References Cited

U.S. PATENT DOCUMENTS

| | | | |
|---|---|---|---|
| 2005/0181074 A1* | 8/2005 | Watson et al. ................. | 424/725 |
| 2005/0287261 A1* | 12/2005 | Zhou et al. .................... | 426/404 |
| 2006/0003029 A1* | 1/2006 | Nash et al. .................... | 424/725 |
| 2007/0031574 A1 | 2/2007 | Han et al. | |
| 2008/0260876 A1* | 10/2008 | Benhamou et al. ........... | 424/756 |
| 2010/0069674 A1 | 3/2010 | Groom et al. | |
| 2011/0318436 A1* | 12/2011 | Mitra et al. ................... | 424/754 |

FOREIGN PATENT DOCUMENTS

| | | | |
|---|---|---|---|
| CN | 1085743 A | * | 4/1994 |
| CN | 101732543 A | * | 6/2010 |
| JP | 57155982 A | * | 9/1982 |
| JP | 02027959 A | * | 1/1990 |
| KR | 20000060990 A | * | 10/2000 |
| KR | 2003062769 A | * | 7/2003 |
| KR | 889051 B | * | 3/2009 |

OTHER PUBLICATIONS

Yamazaki et al. Nippon Shokuhin Kagaku Kogaku Kaishi. 2008. vol. 55, No. 9, pp. 410-415, BIOSIS Abstract enclosed.*
0210/CHE/2004, Compositions and Methods Containing *Allium sativum* Linn. (Garlic) Naturally Enriched With Organic Selenium Compounds for Nutritional Supplementation, Mar. 10, 2004.

* cited by examiner

*Primary Examiner* — Chris R Tate
(74) *Attorney, Agent, or Firm* — Innovation Capital Law Group, LLP; Vic Y. Lin; Joseph G. Chu

(57) ABSTRACT

The present invention relates to a garlic formulation enriched with sulphur containing amino acids and a process for enriching sulphur containing amino acids in garlic. The sulphur containing amino acids includes S-allylcysteine, S-methylcysteine, and S-allylmercaptocysteine. The percentage of enriched garlic concentrate after processing is in the range of 7.5-9.5%. The garlic formulation is useful in the treatment of Diabetes Mellitus (DM) and prevention of tissue and organ damage that occurs frequently in diabetic patients.

10 Claims, No Drawings

GARLIC FORMULATION AND A PROCESS FOR PREPARING THE SAME FOR TREATMENT OF DIABETES

FIELD OF INVENTION

The present invention relates to a garlic (*Allium sativum*) formulation, more specifically, to a garlic formulation enriched with sulphur containing amino acids. The present invention also relates to a process for enriching sulphur containing amino acids in garlic. The garlic formulation is useful in the treatment of Diabetes Mellitus (DM) and prevention of tissue and organ damage that occurs frequently in diabetic patients.

BACKGROUND OF INVENTION

Diabetes mellitus (DM) is one of the most challenging diseases facing health care professionals. It is defined as a disorder of carbohydrate metabolism caused by absence or deficiency of insulin, insulin resistance or both, ultimately leading to a cluster of disorders (Neslihan Toyran et al., 2006). DM has attained epidemic proportions in most parts of the world, including developing countries. More than 220 million people worldwide have diabetes and this number is likely to be more than double by the year 2030 (WHO, 2010). It is the third leading cause of death in many developed countries. The long-term complications of diabetes are more damaging. The management of diabetes mellitus is considered a comprehensive problem and successful treatment is yet to be discovered.

Garlic (*Allium sativum*) is widely cultivated and consumed worldwide, and its beneficial effects have been known for thousands of years. It has been considered to increase longevity and to confer stamina and physical strength. It has been used empirically as a vermifuge, antiseptic, antimicrobic, antipyretic, and analgesic. The scientific community has now become interested in the pharmacologic properties of *Allium* vegetables and their chemical constituents, particularly with regard to their effects on the cardiovascular system and in the prevention of cancer. The medical uses of garlic have a long history. Garlic has been used not only as a flavouring agent but also as a medicine. Interest in the potential benefits of garlic has origins in antiquity and is one of the earliest documented examples of plants used for maintenance of health and treatment of disease. Hundreds of chemical substances are present in fresh, dried or extracts of garlic.

Indian Patent Application 210/CHE/2004 discloses a method of preparing concentrates from garlic bulbs enriched with organic selenium, for use as a nutritional supplement.

US20070031574 describes a method of producing aged garlic using hot air treatments of different temperature ranges in order to produce S-arylcysteine and increase polyphenol content.

US20100069674 describes a method of producing polysulfides by adding elemental sulphur to a plant extract containing Allicin.

Aging is an important step in processing garlic to obtain various biomedical components. Aging is generally carried out by soaking garlic in 15-20% ethanol for 20 months in stainless steel tanks and the filtrate is concentrated at low temperatures. Since 20 months aging is a prolonged period for industrial scale production, a process for lesser duration was standardised.

Accordingly, there exists a need to develop a safe and effective formulation, which can be manufactured on a large scale in a short duration, and can help in the control and management of blood sugar levels and associated complications in patients suffering from diabetes mellitus.

OBJECTS OF INVENTION

One or more of the problems of the conventional prior art may be overcome by various embodiments of the system and method of the present invention.

The primary object of the present invention is to provide garlic (*Allium sativum*) formulation enriched with sulphur containing amino acids.

It is another object of the present invention to provide a process for enriching sulphur containing amino acids in garlic.

It is another object of the present invention, wherein the garlic formulation is useful in the treatment of Diabetes Mellitus (DM) and prevention of tissue damage that occurs frequently in diabetic patients.

It is another object of the present invention, wherein the garlic formulation is enriched with sulphur containing amino acids such as S-allylcysteine, S-methylcysteine, S-allylmercaptocysteine and other allied compounds.

It is another object of the present invention, wherein the enriched concentration of S-allylcysteine is increased to about 7.5-9.5% after processing from an initial concentration of about 0.2%.

It is another object of the present invention, wherein the garlic formulation is processed into powder and further pharmacologically modified to a final product, which is in tablet, caplet or capsule form.

It is another object of the present invention, wherein pH range at which the final product is soluble is in the range of 6.5-7.5.

It is another object of the present invention, wherein the final product is administered orally.

SUMMARY OF INVENTION

Thus according to the basic aspect of the present invention there is provided a method of preparing dry product of enriched garlic containing amino acid concentrates comprising the steps of:

Subjecting peeled garlic cloves in a container to dehydration to a safe moisture content by hot air treatment at a specific temperature;

Storing the dehydrated garlic in room temperature in airtight container for a specific period;

Soaking the dehydrated stored garlic in 20% ethanol for a specific period and grinding to fine paste in a blender;

Drying the garlic paste in a vacuum dryer at a specific temperature; and

Pulverising the dried paste, wherein the pulverised garlic product is enriched with sulphur containing amino acids, wherein percentage of enriched garlic concentrate is in the range of 7.5-9.5%, and wherein the pulverised garlic is pharmacologically modified to tablets, caplets and/or capsules to yield a final product.

It is another aspect of the present invention, wherein the sulphur containing amino acids includes S-allylcysteine, S-methylcysteine, and S-allylmercaptocysteine.

It is another aspect of the present invention, wherein the concentration of S-allylcysteine before processing is approximately 0.2%.

It is another aspect of the present invention, wherein the enriched concentration of S-allylcysteine after processing is in the range of 7.5%-9.5%.

It is another aspect of the present invention, wherein the safe moisture content is 0.06 g water/g dry mass.

It is another aspect of the present invention, wherein percentage weight of the garlic paste used is in the range of 96%-98%.

It is another aspect of the present invention, wherein the specific temperature is below 40° C.

It is another aspect of the present invention, wherein the dehydrated garlic is stored in the container approximately for a period of 10 months.

It is another aspect of the present invention, wherein the dehydrated stored garlic is soaked in ethanol approximately for a period of 50-75 days.

It is further aspect of the present invention, wherein pH range at which the final product is soluble is in the range of 6.5-7.5.

DETAILED DESCRIPTION OF THE INVENTION

The present invention as discussed hereinbefore relates to a garlic formulation enriched with sulphur containing amino acids especially S-allylcysteine. The present invention also relates to a process for manufacturing the said garlic formulation.

In the present invention, the garlic cloves are peeled and dried before processing. Stepwise standardization of protocol is carried for dehydrating, treating the garlic and processing before developing the final formulation.

Fresh garlic bulbs in size ranging from 1.5 to 3 inches in diameter are used for the present invention. The initial moisture content of garlic varied from 1.63 to 1.88 g water/g dry mass. A vacuum oven method is used to determine the initial moisture content of the garlic cloves. The process for preparing the garlic formulation of the present invention involves cleaning the garlic bulbs gently and separating the cloves carefully to avoid any damage. The separated garlic cloves are peeled. Soft and cracked cloves are removed to avoid garlic odor and its interference in the formation of S-allylcysteine and other allied compounds. The unpeeled cloves are stored in room temperature. The peeled garlic cloves without any nicks or damage are kept in steel bins/container and dehydrated by subjecting it to hot air treatments below 40° C. The initial moisture content is reduced to a safe moisture content of 0.06 g water/g dry mass by the above step. The dehydrated garlic is then stored in normal room temperatures in suitable airtight containers for a period of 10 months. The next step involves soaking the dehydrated stored garlic in 20% ethanol for 50-75 days in stainless steel containers at room temperatures. The percolated garlic is ground to fine paste in blender and dried in a vacuum dryer at <40° C. 96-98% wt of garlic paste is used in the preparation of the formulation and the dried paste pulverised. The processing of garlic at low temperatures (i.e. below 40° C. at constant temperature) increases the mild, staple, safe and beneficial compounds in garlic. The garlic powder/pulverised garlic is enriched with compounds such as S-allylcysteine, S-methylcysteine, S-allylmercapto cysteine and other allied compounds. The concentration of S-allylcysteine was 0.2% before processing and this is increased to about 7.5 to 9.5% after processing.

The processed garlic powder is pressed to caplets or tablets of 500 mg and 1 gm. The garlic powder can also be pharmacologically modified to capsules. The pH range at which the tablet/final product is soluble is in the range of 6.5-7.5. The garlic formulation at different dosages is effective in controlling blood glucose levels in conditions of Diabetes Melitus (DM). Tissue damage in pancreas, liver, kidney etc occurs frequently in diabetic patients. The formulation possesses strong antioxidant activity that helps prevent the body from formation of free radicals that can cause tissue damage. The present formulation acts upon the enzymes involved in various metabolic pathways in conditions of diabetic mellitus and tissue/organ damage. The route of administration is oral.

The garlic tablet at the said dosages was subjected to efficacy studies in diabetic animal models. For the efficacy studies on diabetes, studies were carried out using male Wistar albino rats (150-200 g). The animals were grouped and housed in polyacrylic cages with not more than six animals per cage and maintained under standard laboratory conditions (temperature 25°±2° C.) with dark and light cycle (12/12 h). The animals were fed with standard pellet diet supplied by Hindustan Lever Ltd., India and fresh water ad libitum. All the animals were acclimatized to laboratory condition for a week before commencement of experiment. Six animals were divided into five groups for further experiments.

Experimental Design for Efficacy Studies on Diabetes and Tissue Damage:

Rats were randomly allocated to five groups. Diabetes was induced by a single intraperitoneal injection of 120 mg/kg of Streptozotocin (STZ) in citrate buffer (0.1 M, pH 4.5). Group I consisted of normal healthy rats that were administered 1 ml/kg of 0.5% carboxy methylcellulose (CMC) solution orally. Group II consisted of diabetic rats used as control and were administered orally 1 ml/kg of 0.5 carboxy methylcellulose solution. Groups III consisted of diabetic rats treated daily with oral administration of 10 mg/kg of glibenclamide. Group IV consisted of diabetic rats treated orally with 500 mg of tablet suspended in 0.5% carboxy methylcellulose solution. Group V consisted of diabetic rats treated orally with 1000 mg of tablet suspended in 0.5% carboxy methylcellulose solution.

All the test drugs were administered for 21 days. Blood glucose levels were estimated on the $1^{st}$, $3^{rd}$, $7^{th}$, $14^{th}$ and $21^{st}$ day by collecting tail vein using glucometer during drug treatment. On the $22^{nd}$ day, the blood was collected for biochemical estimation by sinus puncture under anesthesia.

The animals were sacrificed by cervical dislocation and organs were removed for histopathological studies.

The Results Obtained are as Follows:

Table 1 shows the average blood glucose concentrations of the five groups of mice. Group IV and V initially showed less anti diabetic activity when compared to standard drug, but from the $7^{th}$ day onwards the formulations showed significant ($P<0.001$) anti diabetic activity which is equipotent to that of standard glibenclamide.

TABLE 1

The effect of garlic formulation on blood glucose in STZ induced diabetic rats.

| Drug Treatment | Blood Sugar (mg/dl) | | | | |
|---|---|---|---|---|---|
| | 1 Day | 3 Day | 7 Day | 14 Day | 21 Day |
| Normal (0.5% CMC, p.o) | 103.83 ± 3.35*** | 104.00 ± 3.09*** | 99.50 ± 1.49*** | 96.00 ± 2.71*** | 99.83 ± 4.24*** |

TABLE 1-continued

The effect of garlic formulation on blood glucose in STZ induced diabetic rats.

| Drug Treatment | Blood Sugar (mg/dl) | | | | |
|---|---|---|---|---|---|
| | 1 Day | 3 Day | 7 Day | 14 Day | 21 Day |
| Diabetic (STZ 55 mg/kg., i.p) | 287.83 ± 2.68 | 293.83 ± 5.39 | 305.83 ± 4.44 | 310.00 ± 4.54 | 319.00 ± 11.82 |
| Standard (Glibenclamide 10 mg/kg., p.o) | 290.50 ± 3.40 | 210.17 ± 5.12*** | 157.67 ± 5.17*** | 124.50 ± 7.48*** | 113.17 ± 5.57*** |
| 500 gm tablet | 291.67 ± 2.64 | 245.33 ± 4.73* | 163.17 ± 5.01*** | 131.00 ± 6.95*** | 124.17 ± 5.96*** |
| 1 g Tablet | 293.00 ± 4.46 | 214.50 ± 3.69** | 155.67 ± 2.49*** | 127.00 ± 6.28*** | 101.00 ± 5.52*** |

Values are presented as mean ± SEM (n = 6)
*P < 0.05, P < 0.01 and *P < 0.001 Vs Diabetic Control Table 2 shows the body weight development, level of scrum total protein, scrum uric acid and serum creatinine in control and experimental group of rats. There was a significant elevation ($p<0.05$) in uric acid and creatinine with significant decrease in total protein and body weight in STZ diabetic rats when compared with control rats. Administration of garlic formulation tablet tended to bring protein, body-weight, uric acid and creatinine towards near normal range.

TABLE 2

Effects of formulation on Body Weight Development, protein, creatinine and uric acid in control and experimental animals

| Drug Treatment | Body Weight(g) | | Protein (mg/dl) | Creatinine (mg/dl) | Uric acid (mg/dl) |
|---|---|---|---|---|---|
| | Initial | Final | | | |
| Normal (0.5% CMC., p.o) (Group I) | 165.31 ± 1.82 | 182.74 ± 3.66 | 125.3 ± 3.74 | 0.75 ± 0.01 | 1.37 ± 0.06 |
| Diabetic (STZ 55 mg/kg., i.p) (Group II) | 172.18 ± 2.21 | 140.22 ± 2.94$^{a*}$ | 100.8 ± 2.67$^{a***}$ | 1.82 ± 0.03$^{a***}$ | 2.04 ± 0.05$^{a***}$ |
| Standard (Glibenclamide 10 mg/kg., p.o) (Group III) | 163.6 ± 1.42 | 161.13 ± 2.14$^{b*}$ | 126.4 ± 2.84$^{b***}$ | 1.04 ± 0.01$^{b***}$ | 1.57 ± 0.06$^{b***}$ |
| 500 mg/day (Group IV) | 165.39 ± 2.26 | 160.47 ± 3.66$^{b*}$ | 122.8 ± 1.01$^{b***}$ | 1.06 ± 0.03$^{b***}$ | 1.55 ± 0.06$^{b***}$ |
| 1 gm/day (Group V) | 161.85 ± 2.72 | 160.18 ± 2.36$^{b*}$ | 118.8 ± 1.75$^{b***}$ | 0.91 ± 0.01$^{b***}$ | 1.53 ± 0.04$^{b***}$ |

Values are given ± S.E for groups of six animals in each group
Values are statistically significant at p p < 0.01 < *0.001
$^{a}$Group II compared with Group I
$^{b}$Group III, IV and V compared with Group II Table 3 shows the level of haemoglobin, glycated haemoglobin and insulin level in control and experimental animals. A significant reduction ($p<0.05$) in haemoglobin and insulin level and concomitant increase in glycated haemoglobin level was observed in STZ diabetic rats and it was normalized after treatment of garlic formulation. The effect at a dose 1 tablet of garlic formulation was more pronounced than that of the dose ½ tablet and brought back all the parameters to near normal.

TABLE 3

Effect of Garlic formulation on Hemoglobin (HB), Glycosylated hemoglobin (HBA₁C) and plasma insulin in control and experimental group of rats

| Drug Treatment | HB (mg/dl) | HBA1C (% Hb) | Plasma Insulin (μU/ml) |
|---|---|---|---|
| Normal (0.5% CMC., p.o) (Group I) | 12.53 ± 0.05 | 0.15 ± 0.004 | 17.7 ± 0.38 |
| Diabetic (STZ 55 mg/kg., i.p) (Group II) | 9.03 ± 0.14a*** | 0.26 ± 0.006a*** | 11.2 ± 0.23$^{a***}$ |
| Standard (Glibenclamide 10 mg/kg., p.o) (Group III) | 11.94 ± 0.23$^{b***}$ | 0.17 ± 0.008$^{b***}$ | 16.4 ± 0.27$^{b***}$ |
| 500 mg /day (Group IV) | 12.45 ± 0.08$^{b***}$ | 0.18 ± 0.006$^{b***}$ | 17.9 ± 0.36$^{b***}$ |
| 1000 mg/day (Group V) | 11.95 ± 0.23$^{b***}$ | 0.17 ± 0.004$^{b***}$ | 16.8 ± 0.31$^{b***}$ |

Values are given ± S.E for groups of six animals in each group
Values are statistically significant at *p < ***0.001
$^{a}$Group II compared with Group I
$^{b}$Group III, IV and V compared with Group II Table 4 depicts the activities of serum aspartate aminotransferase (AST), alanine aminotransferase (ALT) and alkaline phosphatase (ALP) in control and experimental groups of rats. There was a significant elevation in scrum AST, ALT and ALP in STZ diabetic rats when compared with control rats. Oral treatment of garlic formulation tablet tended to bring AST, ALT and ALP towards near normal levels. The effect at a dose 1000 mg tablet of garlic formulation was more pronounced than that of the dose 500 mg tablet and brought back all the parameters to near normal.

TABLE 4

Effects of formulation on serum AST (Aspartate aminotransferase), ALT and ALP in control and experimental animals

| Groups | AST µmoles of pyruvate/h/mg/of protein | ALT | ALP µmoles of phenol liberated/min/mg of protein |
|---|---|---|---|
| Normal (0.5% CMC., p.o) (Group I) | 58.5 ± 1.92 | 43.4 ± 0.68 | 161.7 ± 2.34 |
| Diabetic (STZ 55 mg/kg., i.p) (Group II) | 230.5 ± 8.37 a*** | 77.9 ± 1.05 a*** | 223.7 ± 2.69 a*** |
| Standard (Glibenclamide 10 mg/kg., p.o) (Group III) | 161.0 ± 64.0 $^{b***}$ | 56.4 ± 1.54 $^{b***}$ | 171.9 ± 4.07 $^{b***}$ |
| 500 mg/day (Group IV) | 95.7 ± 3.5 $^{b***}$ | 43.8 ± 1.14 $^{b***}$ | 163.5 ± 0.96 $^{b***}$ |
| 1 gm/day (Group V) | 88.5 ± 3.5 $^{b***}$ | 41.4 ± 0.78 $^{b***}$ | 160.4 ± 1.77 $^{b***}$ |

Values are given ± S.E for groups of six animals in each group
Values are statistically significant at *p < ***0.001
a Group II compared with Group I
$^{b}$ Group III, IV and V compared with Group II
Units: The enzyme activities are expressed as: AST and ALT µmoles of pyruvate/h/mg/of protein; ALP µmoles of phenol liberated/min/mg of protein.

The above results indicated that the garlic formulation of the present invention reverses the adverse effect of hyperglycemia and provides an insight into the pathogenesis of diabetic complication and may be used to advantage in therapeutic approaches.

I claim:

1. A method of preparing dry product of enriched garlic containing amino acid concentrates comprising the steps of:

Subjecting peeled garlic cloves in a container to dehydration to a safe moisture content by hot air treatment at a specific temperature;

Storing the dehydrated garlic in room temperature in airtight container for a specific period;

Soaking the dehydrated stored garlic in 20% ethanol for a specific period and grinding to fine paste in a blender;

Drying the garlic paste in a vacuum dryer at a specific temperature; and

Pulverising the dried paste, wherein the pulverised dried garlic paste is enriched with sulfur containing amino acids, wherein the percentage of sulfur-containing amino acids within the pulverized garlic paste is in the range of 7.5-9.5%, and forming the pulverised garlic into a pharmaceutical form selected from the group consisting of tablets, caplets and/or capsules to yield a final product.

2. The method as claimed in claim 1, wherein the sulfur containing amino acids includes S-allylcysteine, S-methylcysteine and S-allylmercaptocysteine.

3. The method as claimed in claim 2, wherein the concentration of S-allylcysteine before processing is approximately 0.2%.

4. The method as claimed in anyone of claims 1 to 3, wherein the sulfur containing amino acids consists of S-allylcysteine.

5. The method as claimed in claim 1, wherein the safe moisture content is 0.06 g water/g dry mass.

6. The method as claimed in claim 1, wherein percentage weight of the pulverized dried garlic paste used to form the pharmaceutical form selected from the group consisting of tablets, caplets and or capsules is in the range of 96%-98%.

7. The method as claimed in claim 1, wherein the steps of subjecting peeled garlic cloves in a container to dehydration to a safe moisture content by hot air treatment at a specific temperature; storing the dehydrated garlic in room temperature in airtight container for a specific period; soaking the dehydrated stored garlic in 20% ethanol for a specific period and grinding to fine paste in a blender; drying the garlic paste in a vacuum dryer at a specific temperature; and pulverising the dried paste are performed at a specific temperature is below 40° C.

8. The method as claimed in claim 1, wherein the dehydrated garlic is stored in the container approximately for a period of 10 months.

9. The method as claimed in claim 1, wherein the dehydrated stored garlic is soaked in ethanol approximately for a period of 50-75 days.

10. The method as claimed in claim 1, wherein pH range at which the tablets, caplets and/or capsules is soluble in aqueous solution is in the range of 6.5-7.5.

* * * * *